United States Patent [19]

Allred

[11] 4,097,373

[45] Jun. 27, 1978

[54] HIGH SPEED PARTICLE SORTER USING A FIELD EMISSION ELECTRODE

[76] Inventor: John Caldwell Allred, 1300 Antigua La., Houston, Tex. 77058

[21] Appl. No.: 780,281

[22] Filed: Mar. 23, 1977

[51] Int. Cl.$^2$ ............................................. B07C 5/342
[52] U.S. Cl. .............................. 209/111.5; 209/74 R; 209/3; 356/39; 346/75
[58] Field of Search ..................... 209/3, 4, 73, 74 R, 209/74 M, 111.5, 111.6, 111.7 T; 250/222 CP; 356/39; 324/71 CP; 346/75; 235/92 CP

[56] References Cited

U.S. PATENT DOCUMENTS

| | | | |
|---|---|---|---|
| 3,656,174 | 4/1972 | Robertson | 346/75 |
| 3,710,933 | 1/1973 | Fulwyler et al. | 356/39 X |
| 3,826,364 | 7/1974 | Bonner et al. | 209/111.7 T X |
| 3,893,126 | 7/1975 | Ascoli et al. | 346/75 X |

OTHER PUBLICATIONS

"A New Multiparameter Separator for Microscopic Particles and Biological Cells"; Review of Scientific Instr., vol. 44, Sep. 1973.
"Fluorescence – Activated Cell Sorting"; Scientific American, vol. 234, No. 3, Mar. 1976.

*Primary Examiner*—Robert B. Reeves
*Assistant Examiner*—Joseph J. Rolla

*Attorney, Agent, or Firm*—Arthur M. Dula; Ned L. Conley; Murray Robinson

[57] ABSTRACT

The present invention sorts small particles by subjecting them to a charging and motivating field produced by a single electrode. The magnitude of the charge placed on the particle passing the electrode is a controlled function of observed particle parameters. The amount of charge placed on the small particle in this manner determines the amount of deflection imparted to the particle's trajectory. Once the particle has been deflected in accordance with its observed parameter, the particle may be collected for further study. It will be appreciated that this version of the present invention deflects the small particle by applying a force to it at some angle to its direction of movement. The particle's movement will generally be impelled by the accelerative force of the fluid stream along a line between the end of a droplet producing nozzle and a collection station. The application of a variable force, dependent on particle parameters, at some angle, usually normal, to this line results in movement of the particle in a plane defined by the line from the droplet generator to the collector and a point not on the line determined by the charging and motivating electrode. Absent other exterior forces, such as gravity, all modulation of the particle's trajectory takes place within this plane.

13 Claims, 4 Drawing Figures

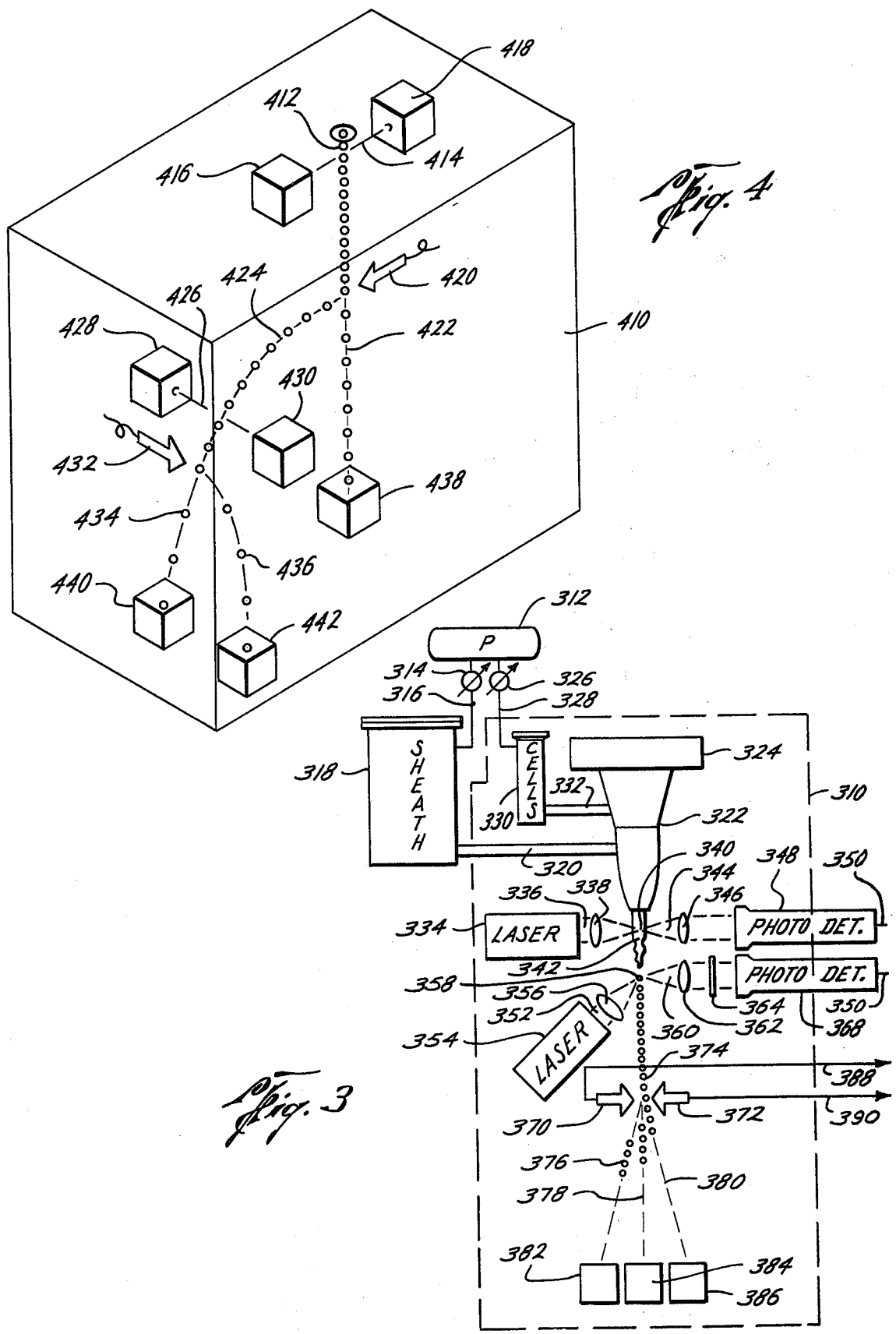

HIGH SPEED PARTICLE SORTER USING A FIELD EMISSION ELECTRODE

BACKGROUND OF THE INVENTION

1. Field of the Invention

The present invention relates generally to methods and apparatus for sorting particles using fields of force and more specifically relates to methods and apparatus for sorting small particles on the basis of a sensed parameter using an electric field.

2. Background of the Prior Art

It has long been known that the trajectory of a charged body moving in a uniform field will be deflected if a second field is generated orthogonal to the first field.

U.S. Pat. No. 2,646,880, for example, shows an apparatus that accelerates small particles uniformly under the influence of gravity and sorts them with an electric field. In this apparatus the small particles have a mass that responds to a gravity field. An electrode places an electric charge on the mass in response to a signal from a photocell and the charged particle is then acted on by the electric field emanating from a plurality of charged plates whose field intensity is constant. The charged particles are deflected into a collecting dish while the uncharged particles fall undeflected into another collection area.

Functionally, the prior art teaches the charging of small particles in response to at least one observed parameter of the particle. The particle is then allowed to fall under the influence of gravity between a plurality of charged plates which deflect its path.

Alternatively, the amount of charge placed on the particle can be varied as an analog of one or more observed parameters (see U.S. Pat. No. 3,380,584 issued Apr. 30, 1968 to Fulwyler); the charge can be self-induced by the particle's movement (see U.S. Pat. No. 3,656,171, issued Apr. 11, 1972 to Robertson); a plurality of particle parameters may be sensed (see U.S. Pat. No. 3,710,933, issued Jan. 16, 1973 to Fulwyler, et al.); or the polarity of the charge placed on the particles may be made a function of the sensed particle parameter (see U.S. Pat. No. 3,826,364, issued July 30, 1974 to Bonner, et al.).

The rapid development of these small particle sorters has accompanied the rise of a need to sort biological objects such as cells and chromosomes. The usefulness of such sorters and a good description of the parameters used by them to discriminate between particles may be appreciated by reading "A New Multiparameter Separator for Microscopic Particles and Biological Cells" in volume 44 of the *Review of Scientific Instruments* (September, 1973 at page 1301). This reference also discusses the electrical control technology that is well-known by those skilled in the prior art for controlling the prior art's charging electrodes.

An excellent overview of the prior art is found in "Fluorescence-Activated Cell Sorting" in Volume 234, number 3 of *Scientific American* (March 1976 at page 108).

All of the methods and apparatus taught by the prior art contain a fundamental limitation that greatly reduce their usefulness in sorting biological materials. This is a limit on sorting rate that is caused by the use of at least one electrode to charge the particle followed by at least two other electrodes which develop electric fields to deflect the particle.

A particle, according to the prior art, must move through a charging field, which takes time, be transported to a displacing field, which takes more time and then pass through a displacing field, which takes still more time. If more than one particle at a time moves through these fields, the prior art methods missort the additional particles because they would be sorted with the sensed particle. The prior art is thus limited to sorting rates of a few hundred cells per second (see the cited *Review* article, on page 1302 and *Scientific American* on page 111).

The prior art teaches production of approximately 45,000 droplets per second, but can only sort a few hundred to a few thousand particles per second. Thus a technique of using multiple "dummy drops" to insure isolation of each cell into a single sorted droplet has been developed. This greatly limits the number of cells that can be sorted in a given time by prior art methods.

Nothing in the prior art teaches or suggests the use of a single electrode to charge and deflect particles, nor is there any suggestion that sorting rates can be increased by the use of a single charge/sort process. Since the sorting rate is critically important to the practical utilization of these devices in biological applications this is a major problem that has long defied solution. The best prior art devices, for example, would have to operate continuously for about 1 year to sort an ounce of cells. It may be readily appreciated that this limits their usefulness, especially where the sorting is being done in an attempt to isolate cells that possess statistically rare characteristics.

SUMMARY OF THE INVENTION

The present invention sorts small particles by subjecting them to a charging and motivating field produced by a single electrode. The magnitude of the charge placed on the particle passing the electrode is a controlled function of observed particle parameters. The amount of charge placed on the small particle in this manner determines the amount of deflection imparted to the particle's trajectory. Once the particle has been deflected in accordance with its observed parameter, the particle may be collected for further study. It will be appreciated that this version of the present invention deflects the small particle by applying a force to it at some angle to its direction of movement. The particle's movement will generally be impelled by the accelerative force of the fluid stream along a line between the end of a droplet producing nozzle and a collection station. The application of a variable force, dependent on particle parametes, at some angle, usually normal, to this line results in movement of the particle in a plane defined by the line from the droplet generator to the collector and a point not on the line determined by the charging and motivating electrode. Absent other exterior forces, such as gravity, all modulation of the particle's trajectory takes place within this plane.

In an alternative embodiment of the present invention one or more additional charging and motivating electrodes similar to the first charging and motivating electrode is placed out of the plane defined above. Its electric field is modulated in response to another sensed parameter of the particle being sorted. In this case, given that the two or more motivating electrodes are placed the same distance from the droplet-producing nozzle, the field of this second electrode adds vectorially to the field of the first electrode to deflect the trajectory of said particle out of the plane described above.

Although these other electrodes may be placed at any angle that is out of the plane defined by the first electrode and the particle's unaltered trajectory, it may readily be appreciated that the second electrode will normally be mounted orthogonal to both the first electrode and to the line described by the particle's undisturbed path. This arrangement allows the particle to be sorted by deflecting its path through a three dimensional volume. Depending upon the charges placed on the two electrodes, the particle will impinge upon the collector plane at some predictable coordinate. A plurality of collection tubes can be located in this plane.

Functionally, the motivating electrode acts to impart a charge to the free falling particle by means of field emission. The particle undergoes field charging very rapidly because of the high field strengths, around 4,000 kilovolts/centimeter, required to initiate field emission. Because the particle is charged to the same electric polarity as the charging electrode, the charging electrode will tend to repel the particle as it becomes charged. The charging particle will be more or less repelled by the field surrounding the field emission electrode. If two electrodes are used synergistically, then the force experienced by the particle is a function of the vector sum of the fields generated by the two electrodes.

Because of the field's strength surrounding the charging and motivating electrode in the present invention, the particle is charged and mobilized very rapidly. As a result of this rapid mobilization, sorting may be accomplished by the present invention at a rate of at or above 100,000 particles per second.

This rate of sorting for the present invention is not limited by the flight time between a plurality of electrodes as is the prior art, but rather depends upon the rate of field charging that is possible for the particle in the field generated by the electrode. The present invention may be operated in helium, so the sonic velocity of the sort stream will increase to permit faster sorting.

BRIEF DESCRIPTION OF THE DRAWINGS

FIG. 3 is a highly schematic functional diagram illustrating an embodiment of the present invention using a plurality of field emission electrodes at the same point in the particle stream;

FIG. 4 is a highly schematic functional block diagram of an apparatus capable of practicing the present invention illustrating the use of a plurality of field emission electrodes to sequentially sort a particle stream.

DESCRIPTION OF THE PREFERRED EMBODIMENT

Before beginning the detailed description of the preferred embodiment, the inventor wishes to reference the reader of this specification to U.S. Pat. No. 3,710,933 for a very detailed discussion of how droplets containing cells are produced. The specification of this patent also contains a description of the signal processing electronics utilized in these devices. U.S. Pat. No. 3,380,584 also has extremely detailed functional block diagrams and schematics showing how a typical set of electronics would be constructed for the present invention. Finally, U.S. Pat. No. 3,826,364 describes in fine detail, including schematics and logic signal timing diagrams together with detail block diagrams, the specific electronics shown in part in FIG. 3 of the present specification. The inventor of the present invention does not believe it would materially advance or improve this specification for him to reiterate all of the well known prior art concerning, for example, the use of lasers and photodetectors to sense particle parameters and the associated electronics required to present a modulated electrical signal that is a function of these sense parameters to an electrode. Those skilled in the art would find the construction of such apparatus to be mechanically interesting, but intellectually trivial. The reader is directed to the referenced U.S. Patents for any details not supplied in this specification.

Figure 1:
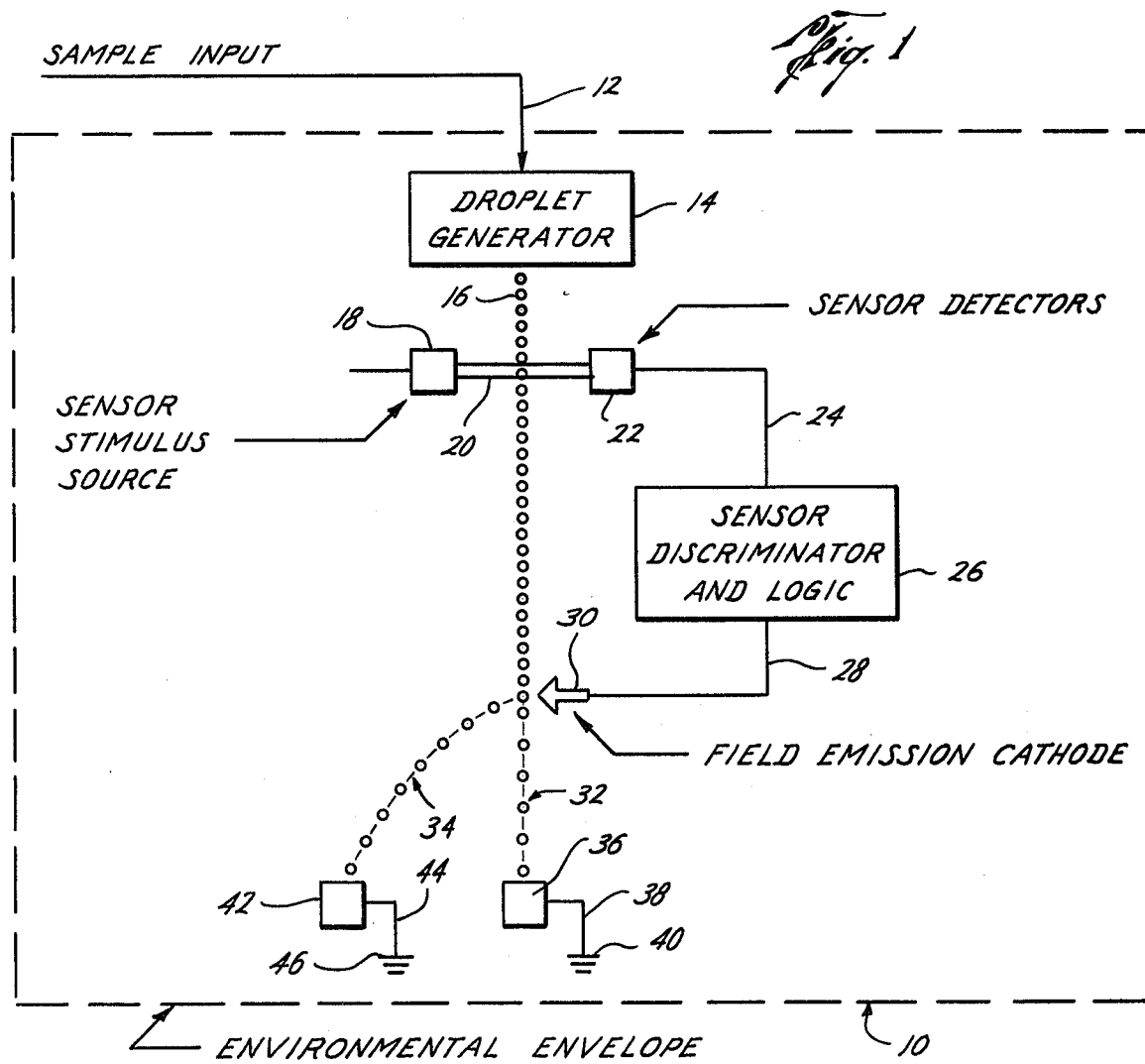
FIG. 1 is a schematic block diagram of an apparatus capable of performing the present invention.

FIG. 1 is a simplified functional block diagram showing the major elements required of an apparatus to practice the present invention. Environmental envelope 10 is a hermetic chamber containing helium at reduced pressure. A sample containing cells or other particles to be sorted is introduced into environmental envelope through sample input line 12. Droplet generator 14, also within environmental envelope 10 contains the required ultrasonic droplet generator and sheath supply reservoirs to form small droplets, approximately 300 microns in diameter, spaced approxmately 300 microns apart. Each of these droplets may contain a particle to be sorted, for example a human red blood cell which has a major axis diameter of 7.5 microns and is approximately 2 microns thick. This stream of particle containing droplets 16 passes out the exit nozzle of droplet generator 14.

Sensor stimulus source 18 generates a source of stimulus directed so as to interact with the droplets of stream 16. This stimulus source may be, for example, an argon laser or a helium neon laser. Alternatively it could be any other source of stimulus capable of detecting some measurable parameter of the particles contained in particle drop stream 16. Stimulus beam 20 comes from the output of stimulus source 18, intersects droplet stream 16 so as to stimulate one drop at a time, and then impinges on sensor detectors 22. Sensor detectors 22 may be any detector capable of being affected by the stimuli generated by stimulus source 18 after its modulation by the particles within droplet stream 16.

Sensor detector 22 is connected by line 24 to the sensor discriminator and logic 26. Sensor discriminator and logic 26 represents the electronics that sort the signal produced by sensor detector 22 out from noise and determine electronically when a desired state of modulation has been impressed on the stimulus generated by stimulus source 18 by the particle in the particular droplet of droplet stream 16 being irradiated by stimulus beam 20. Sensor discriminator and logic 26 generates a output high potential wave form which is a function of the sensed parameter being pressured by sensor detector 22. Any competent electrical engineer would be capable of designing specific circuits for specific applications, therefore the present specification shows these electronics in their most generalized form.

The high potential wave form generated by sensor discriminator and logic 26 in response to the sensed parameter of a particle travels through output line 28 to field emission cathode 30, which is represented by a large arrow. Field emission cathode 30 is a very tiny pointed needle whose tip diameter is on the order of 10 microns in radius. When a high electric potential is applied to such an electrode its tip experiences an extremely high field intensity. When this field potential becomes strong enough electrons escape from the surface of the field of the electrode and travel out and away from it. This effect is called "field emission." Field emission is well understood by those having skill in the art of electron beam generation and control. If the reader is not familiar with this technology, such electrodes are available commercially from a variety of sources.

The 10 micron tip of field emission cathode 30 is located approximately 500 microns from the center of particle stream 16. This place is approximately 350 microns from the outer surface of each of the droplets as they flow past the electrode.

Figure 2:
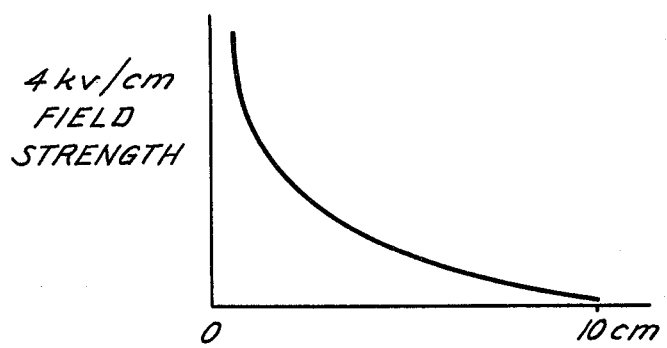
FIG. 2 is a graph showing the relationship between field strength and distance from the field emission cathode.

The electric charge impressed on field emission cathode 30 by sensor discriminator and logic 26 is on the order of $4 \times 10^8$ volts per meter. As is shown in FIG. 2, this field strength falls off very rapidly as a function of distance, but at the extremely close distances described above between the field emission cathode and the particles in the particle stream 16, the electric field acting on the particles, once they become charged, will be approximately $4 \times 10^8$ volts per meter when the apparatus described by the preferred embodiment of the present invention is operating to deflect the trajectory of a particle.

Particle stream 16 branches into two particle streams 32 and 34 downstream of the field emission cathode 30. Particle stream 32 continues the undeflected path of particle stream 16 into collector receptacle 36, which is a conductive cup grounded by line 38 to ground 40.

Deflected particle stream 34 travels in an altered trajectory to collector cup 42, which is a conductive collector cup tied by line 44 to ground 46.

Environmental envelope 10 may be made of any material that is reasonably hermetically sealed and strong enough to contain subatmospheric helium under normal atmospheric pressure. Droplet generator 14, sensor stimulus source 18, sensor detector 22, sensor discriminator and logic 26, field emission cathode 30 are all available commercially. Anyone familiar in the least with flow microfluorometry will know the source of supply for all of these goods.

Functionally, sample input 12 comprises a collection of small particles, for example cells, in solution. Droplet generator 14 acts in a well known way to controllably place these cells into extremely small, 300 micron diameter, droplets. In the prior art, only one cell was placed in every seven to 15 droplets. The present invention is capable of placing one cell in every droplet generated by the ultrasonic droplet generator. The present device also operates at a much higher flow rate than than taught by the prior art. If the present invention operates at a flow rate of 500 meters per second, and the diameter of each droplet is 330 microns, then each droplet will be within the effective operating range of the field emission cathode for approximately $3 \times 10^{-7}$ seconds and $5.6 \times 10^{-10}$ coulomb of electric current will be transferred to the droplet if the field emission cathode is charged to produce a field of $4 \times 10^8$ volts per meter. If the reasonable assumption is made that half of the time spent by the particle in the field is dedicated to acquiring a charge and the other half of the time in the field is dedicated to transferring momentum, then the droplet will be mobilized away from the field emission cathode with a velocity of 12 meters per second. If the flow path between a field emission cathode 30 and collection cup 36 or 42 is 3 meters, then the total separation achieved between droplet stream 32 and droplet stream 34 at the end of the three meter path length is 7.2 centimeters, or a little less than 3 inches. If a one inch separation is acceptable, then the path length utilized by the present invention need be no longer than 1½ meters.

At 500 meters per second the present invention will sort over 800,000 particles per second. This is over 150 times faster than the fastest sorting method taught by the prior art. In order to sort at this rate the droplet generator must operate at 800 kilocycles and the sensor discrimination and logic must have a reaction time of under 1 microsecond. Since nanosecond sensors and electronics are now available commercially from any electronic parts house, the inventor does not believe that this requirement of his invention is beyond the state of the art.

Once the particle containing droplets in stream 16 passes through stimulus beam 20, sensor detector 22 picks up the modulated stimulus and sensor discriminator and logic 26 generates an output wave form that either will or will not impress a high potential on field emission cathode 30 when the sensor particle is within effective range of the field emission cathode. If the particle is to be mobilized, then field potential will be applied to the field emission cathode 30 when the sensed particle is within its effective range and it will be mobilized into stream 34 which terminates in collector cup 42. If the particle is not to be sorted, then it will continue along the trajectory of stream 32 into collector cup 36. Once the particles reach collector cups 42 and 36, their charge is drained off to ground by lines 44 and 38.

It is anticipated that the output of droplet generator 16 will be in very close juxtaposition with stimulus beam 20. Field emission cathode 30 may be located at any point downstream of the stimulus beam. The distance between the stimulus beam 20 and the field emission cathode 30 will be large enough to permit the operation of the sensor discriminator and logic electronics in the flight time of the particle between the two positions. collector cups 42 and 36 will be located sufficiently downstream from field emission cathode 30 to permit the momentum transferred by the field emission cathode to the particles in particle stream 34 to have allowed sufficient separation so that the particles may be separately collected.

FIG. 2 shows a plot of the field strength experienced by a charged particle near a field emission cathode charged to $4 \times 10^8$ volts per meter as a function of the distance between the particle and the 10 micron tip of the field emission cathode. The graph is present in this specification only to show that the field strength falls off strongly with distance. In the example given above in connection with FIG. 1, field emission cathode was located 350 microns from the edge of the particle stream 16 generated by droplet generator 14.

FIG. 3 is a schematic block diagram showing the principal elements of an embodiment of the present invention that uses two field emission electrodes in parallel to sort the particle stream in response to two sensed parameters. The specific apparatus shown in this drawing was taken from U.S. Pat. No. 3,826,364, and the reader is referred to that issued patent for a detailed explanation of its operation.

Environmental envelope 310 contains helium or any other gas whose sonic velocity is high enough that the particle stream does not approach it. The gas may be at a low pressure to aid sorting. A pressure vessel 312 is connected through regulator 314 to line 316 which is connected to container 318, which is adapted to contain a supply of sheath fluid. Sheath fluid reservoir 318 is connected into the pressure envelope 310 by line 310. Reservoir line 320 terminates into ultrasonic nozzle 322 which is driven by transducer 324.

Pressure reservoir 312 is also connected to pressure regulator 326 and line 328 to cell or particle reservoir 330. Cell or particle reservoir 330 is connected to the ultrasonic droplet producing nozzle 322 by line 332. Helium neon laser 334 produces a beam of coherent light 336 which is focused by optical system 338 onto the cell carrying stream 340 within sheath 342. Modulated output 344 passes through optical system 346 into photo detector 348. The output of photo detector 348 goes via line 350 to the electronics that are discussed in connection with the above-referenced issued patent. After the sheath liquid has separated into individual droplets, each of which may contain a cell or other particle, blue light 352 from cadmium argon laser 354 is focused by optical system 356 onto droplet 358. The modulated light flux 360 coming from droplet 358 is collected by optical system 362 and filtered by filter 364 before impinging on photo detector 368. The output of photo detector 368 travels via line 350 to the electronics described in connection with the above-referenced issued patent. First field emission cathode 370 and second field emission cathode 372 are located opposite one another downstream from the lasers and photo detectors. Droplet stream 374 flows between the two field emission cathodes. Each field emission cathode is approximately 300 to 500 microns from the particle stream's boundary. The field emission cathodes 370 and 372, split particle stream 374 into three streams: left stream 376, center stream 378 and right stream 380. Still within environmental envelope 310 these three streams terminate in separate receptacles. Stream 376 terminates in receptacle 382, stream 378 terminates in receptacle 384 and stream 380 terminates in collector cup 386.

Operationally, a pressurized gas in reservoir 312 is regulated by regulators 314 and 326 which differentially pressurize sheath reservoirs 318 and cell reservoir 330, respectively. Both the cell containing solution in line 332 and the sheath solution in line 320 pass into ultrasonic nozzle 322 which is actuated by transducer 324. The frequency of transducer 324 determines the number of droplets generated by the nozzle. Before stream 340 breaks up into droplets, a red light beam from helium neon laser 334 is focused through optics 338 onto the cells passing through the sheath liquid. Some parameter of the cell modulates this light beam and the output modulated beam 334 is focused by optical train 346 into photo detector 348 where it generates an electrical output that is a function of the sensed parameter.

Further downstream the green-blue light from cadmium argon laser 354 passes through optical train 374 and impinges upon a single droplet 358. Some parameter of this droplet modulates the beam and the output modulated beam 360 is focused by optical train 362 and filtered by filter 364 before passing into photo detector 368. Photo detector 368 generates an electrical output 350 which is a function of the sensed parameter of the cell within the droplet.

The information about the cell contained in the modulated output of the two photodetectors as processed by the sensor discriminator and logic electronics is well known to the prior art. Depending on which of two parameters is present, a high potential electric signal is applied to either first field emission electrode 370 by line 388 or second field emission electrode 372 by line 390. Both lines 388 and 390 are functionally connected to the output of sensor discriminator and logic electronics which are well known in the art.

If a high potential is applied to neither electrode 370 nor electrode 372, then the particle continues down particle path 378 and is collected in grounded collection vessel 384. If the sensed stimulus results in potential being applied to field emission cathode 370, then the trajectory of the particle is deflected into particle stream 380 and the particle is collected in grounded collection vessel 386. If the stimulus from photodetectors 348, 368 results in a high potential charge being placed on second field emission cathode 372, then the particle will be mobilized into particle stream 376 and will be collected in rounded collection vessel 382.

For clarity, the two field emission cathodes 370, 372 are shown opposite each other in FIG. 3. A more normal procedure for operating this embodiment of the present invention would be to have the two field emission cathodes set at right angles to one another. Application of varying potentials to these two field emission cathodes could then sort the particle stream into a great number of different containers depending on the differential charge applied to each of the two electrodes. The sensor discriminator and logic electronics for such an apparatus would be far more complex than the simple one, two or three parameter sort described in connection with FIG. 3. The preferred embodiment of the present invention specifically anticipates that it may be possible to perform an analog separation of particles into a continuous spectrum of containers depending on the particular value of sensed properties in the cell, not merely the presence or absence of a sensed value to a particular degree.

FIG. 4 is a highly schematic block diagram illustrating the sequential sorting of a stream of particles by the present invention.

One of the failings of all prior art sorting apparatuses has been that they sort for only a few, up to four, parameters. If a more detailed sort is desired, then it would be necessary to collect a sample and rerun it through the device. As prior art devices were very slow, this procedure was not workable and in fact has not been utilized to any significant degree.

The parallel sorting device described in connection with FIG. 3 above can sort for a large number of different parameters simultaneously. The inventor of the present invention imagines that there will be times when it is desirable to sort a small particle at different points in time, for example when a chemical reaction is taking place within the small particle and different states will occur only at different times. This would necessitate simultaneous parallel sorting and would require the type of sorting illustrated by FIG. 4.

In FIG. 4 environmental envelope 410 contains all of the apparatus there described. For the sake of clarity the pressure vessels, reservoirs, and transducers shown in connection with FIG. 3 have been omitted. The stimuli source generators and sensors are shown in block form and the field emission cathodes are illustrated as large arrows.

A stream of particles to be sorted 412 enters the environmental envelope and encounters stimulus sensing beam 414 passing between first stimulus generator 416 and first stimulus sensor 418. The output of stimulus sensor 418 is functionally connected through sensor and discriminator electronics to first field emission cathode 420. Downstream from first field emission cathode 420 particle stream 412 diverges into particle stream 422 and sorted particle stream 424.

Sorted particle stream 424 encounters a second stimulus beam 416 generated by second stimulus generator 428 and detected by second stimuli sensor 430. The output of second stimuli sensor 430 is functionally connected through sensor discriminator and logic electronics to second field emission electrode 432.

Downstream of secondary field emission electrode 432 sorted stream 424 diverges into stream 434 secondarily sorted stream 436. Stream 422 is collected by ground container 438, stream 434 is collected in grounded container 440, and stream 436 is collected in grounded container 442.

Functionally, the input stream to be sorted 412 comes from an ultrasonic nozzle such as was described in connection with FIG. 3 above. In passing through sensor beam 414 sensor 418 detects a first parameter to be used in sorting the particles in the droplets. First field emission electrode 420 mobilizes all of the droplets except those having the parameter sensed by sensor 418. The droplets containing particles having the sensed parameter are collected in grounded container 438. All other particles are diverted into sorted stream 424.

Sorted stream 424 passes through second sensing beam 426 and second sensor 430 detects a parameter and actuates second sorting electrode 432 to sort stream 424 according to this parameter. The particles having the desired characteristics are sorted into stream 436 then collected in grounded collection container 442. The rest of the particles follow stream 434 into grounded collector container 440.

Any number of such series of sorting stages may be used. Series sorting may also be performed after the parallel sort operation described in connection with FIG. 3 above.

It is believed that the invention in all of its phases has been fully described sufficiently for one skilled in the art to make and use it. It should be pointed out, however, that the scope of the invention is believed to encompass many variations obvious to those having skill in the art of flow microfluorometry. It is therefore desired that the only limitations to the present invention be those found in the appended claims and their legal equivalents.

I claim:
1. An apparatus for analyzing and sorting small particles on the basis of preselected parameters of combinations of preselected parameters comprising
generating means for segregating one of said particles in at least one liquid droplet;
sensing means downstream of said generating means for sensing the presence and absence of said preselected parameter of said particle;
flow means for passing said particles from said generating means to close proximity of a field emission cathode, said cathode being located downstream of said sensing means;
discrimination means responsive to said sensing means and functionally connected to said field emission cathode for selectively establishing a high potential electric field on said field emission cathode when said particle is closely adjacent said cathode if said sensed particle displays said preselected parameter; and
collection means located downstream of said field emission cathode for receiving said particles.

2. An apparatus as in claim 1 including an environmental envelope filled with a gas whose speed of sound is higher than air surrounding said droplet from said generating means to said collection means.

3. An apparatus as in claim 2 where said flow is at a velocity less than the speed of sound in said gas.

4. An apparatus as in claim 3 wherein said gas is at subatmospheric pressure.

5. An apparatus as in claim 1 wherein said generating means is an ultrasonic droplet generator, said sensing means is a laser whose output intersects said particle and is then sensed by a photo detector, said flow means is a stream of droplets emitted by said generator under pressure, said discrimination means is an electrical signal discriminator responsive to said sensor capable of placing a high potential electric charge on said field emission cathode if said sensor detects that said particle displays said preselected parameter; and said collection means is a plurality of grounded collection containers located so as to intercept the terminus of said particle flow both when said electrode is charged and when it is not.

6. An apparatus as in claim 5 where said flow is at the rate of over 100 meters per second, close proximity is less than 0.1 inches and electric field is at least strong enough to initiate field emission of electrons from said cathode.

7. An apparatus as in claim 6 wherein the degree of electrical potential placed on said electrode is a function of the quantative presence of said sensed preselected parameter of said particle.

8. An apparatus as in claim 6 including at least one additional field emission electrode capable of being charged to a high potential in response to the presence of a second sensed parameter of said particle.

9. An apparatus as in claim 8 wherein said second electrode is located and operated in parallel with said first electrode.

10. An apparatus as in claim 8 wherein said second parameter is sensed prior to said particle's passage near said first electrode and a sorted output stream then passes near said second electrode.

11. A method of sorting small particles according to preselected parameter comprising:
sensing said particles to measure said parameter of each particle;
sequentially moving each said particle to near at least one field emission cathode;
placing a high electric potential on said cathode when each said sensed particle is near it if said particle displays said preselected parameter; and
collecting said particles downstream from said field emission cathode.

12. A method as in claim 11 wherein near is within 0.1 inch; high potential is at least strong enough to initiate field emission and said sequential movement is accomplished by creating a high velocity stream of particles.

13. A method as in claim 12 wherein high velocity is any velocity less than the speed of sound in the medium through which said particle stream is passing.

* * * * *